United States Patent [19]
Saitoh et al.

[11] Patent Number: 5,304,062
[45] Date of Patent: Apr. 19, 1994

[54] PROSTHETIC DENTURE PRECURSOR AND METHOD

[75] Inventors: Yoshihiro Saitoh, Neyagawa; Masaki Tamura; Norikazu Kitamura, both of Hirakata, all of Japan

[73] Assignee: UBE Industries, Ltd., Yamaguchi, Japan

[21] Appl. No.: 952,405

[22] Filed: Sep. 30, 1992

[30] Foreign Application Priority Data

Oct. 1, 1991 [JP] Japan ................. 3-320842
Oct. 4, 1991 [JP] Japan ................. 3-323595
Oct. 4, 1991 [JP] Japan ................. 3-323596

[51] Int. Cl.$^5$ .................. A61C 13/00; A61C 13/08; A61C 13/10
[52] U.S. Cl. .................. 433/171; 433/191
[58] Field of Search .................. 433/171, 191, 199.1, 433/213

[56] References Cited

U.S. PATENT DOCUMENTS

| | | |
|---|---|---|
| 3,667,123 | 6/1972 | Huey et al. |
| 3,987,546 | 10/1976 | Trampe et al. |
| 4,267,133 | 5/1981 | Kohmura et al. ........ 433/199.1 X |
| 4,370,133 | 1/1983 | Stempel ........ 433/171 |
| 4,583,947 | 4/1986 | Hazar ........ 433/171 |
| 4,681,543 | 7/1987 | Monroy . |
| 4,705,476 | 11/1987 | Blair ........ 433/171 |
| 4,838,789 | 6/1989 | Tanaka ........ 433/171 |

FOREIGN PATENT DOCUMENTS

1-155842 6/1989 Japan ........ 433/171

OTHER PUBLICATIONS

Patent Abstracts of Japan; vol. 14, No. 571 (C-790) Dec. 19, 1990 & JP-A-22 39 541 (Sogo Shika Iryo).
Patent Abstracts of Japan; vol. 13, No. 417 (C-636) Sep. 14, 1989 & JP-A-11 55 842 (Sogo Shika Iryo).

*Primary Examiner*—John G. Weiss
*Assistant Examiner*—Nicholas D. Lucchesi
*Attorney, Agent, or Firm*—Armstrong, Westerman, Hattori, McLeland & Naughton

[57] ABSTRACT

A prosthetic denture precursor includes at least one artificial tooth having a root portion; and a photopolymerizable denture base material holding the root portion of the at least one tooth, the photopolymerizable denture base material being deformable so that a dentally operative position of the at least one tooth in the denture precursor is adjustable, the photopolymerizable denture base material irreversibly hardening upon exposure to light so that the at least one tooth is rigidly fixed to the hardened denture base material. A method for manufacturing and using the precursor is described. This method simplifies conventional procedures of making a denture device by omitting steps of making a wax denture.

2 Claims, 2 Drawing Sheets

PROSTHETIC DENTURE PRECURSOR AND METHOD

BACKGROUND OF THE INVENTION

The present invention relates to a prosthetic denture precursor and a method for manufacturing and using the prosthetic denture precursor.

A currently used prosthetic denture device has a denture base formed of a resin material, and a set of individual teeth are set onto the resin material. An acrylic resin is common among possible resin materials for a denture base.

According to a conventional method for making a denture device, a custom mold of a patient's mouth is prepared from an impression. A wax denture is made on the custom mold, and the wax denture is then embedded in an embedding material in a flask. After the embedding material hardens in the flask, the wax is removed by hot water to leave a cavity having a shape of a denture base. Into the cavity was added a doughy mixture of acrylic monomers and acrylic polymers, which resins are then polymerized and hardened upon heating. During the polymerization step the resin in the cavity may be pressurized to give a better conformity of the resin. A denture device made by this conventional method can give an accurate, detailed shape, especially when a suitable wax material is used.

To form a denture base consisting of an acrylic resin by this method, however, involves many steps, and the method is troublesome for a dentist. A patient also may find this method inconvenient because the method may require frequent visits to a dentist.

SUMMARY OF THE INVENTION

In an attempt to simplify the conventional procedures to make a prosthetic denture device, the present invention provides a prosthetic denture precursor, comprising at least one artificial tooth and a photopolymerizable denture base material. The artificial tooth has a root portion and a photopolymerizable denture base material holds the root portion of the tooth. The photopolymerizable denture base material is deformable so that a dentally operative position of the tooth in the denture precursor is adjustable. The photopolymerizable denture base material irreversibly hardens upon exposure to light so that the tooth is rigidly fixed to the denture base.

Preferably the photopolymerizable material has a composition including a photopolymerizable acrylic resin.

Preferably the tooth contains an acrylic resin and the photopolymerizable denture base material has a composition including a photopolymerizable acrylic resin having a polymerizable component so that a part of the polymerizable component is able to diffuse into the tooth, whereby upon exposure to light the tooth is chemically bonded by polymerization of the polymerizable component to the hardened denture base material.

The photopolymerizable material may have a composition including a compound having at least one species selected from a group consisting of methylmethacrylate, ethylmethacrylate, triethylene glycol dimethacrylate, diethylene glycol dimethacrylate, ethylene glycol dimethacrylate, 2, 2-bis[4-(2-hydroxy-3-methacryloxypropoxy)phenyl]propane, and di(methacryloxy)trimethylhexamethylenediurethane.

According to another aspect of the present invention, there is provided a method for manufacturing and using a prosthetic denture precursor. This method of making a prosthetic denture device simplifies the elaborate conventional procedures of making a denture device by omitting steps of making a wax denture. A photopolymerizable material and at least one artificial tooth having a root portion are placed in at least one mold. Preferably the tooth contains an acrylic resin. The photopolymerizable material is deformable. Preferably the photopolymerizable denture base material has a composition including a photopolymerizable acrylic resin having a polymerizable component. The photopolymerizable material is formed into a denture base having the tooth embedded therein, and the denture precursor is removed from the mold. Preferably a part of the polymerizable component is able to diffuse into an acrylic tooth. The denture precursor is placed in contact with a spacer which is in contact with a custom mold. The tooth is adjusted to a dentally operative position. Preferably the denture base is adjusted so as to conform to the spacer. The denture base is irreversibly hardened by exposure to light so that the tooth is rigidly fixed to the hardened denture base. Preferably by exposure to light the acrylic tooth is chemically bonded by polymerization of the polymerizable component to the hardened denture base. The spacer is removed from the custom mold and a resin material is placed into the recess occupied by the spacer so that the resin material conforms to both the custom mold and the denture base in the denture precursor. The resin material is hardened so that the resin material integrates into the denture base.

DESCRIPTION OF THE PREFERRED EMBODIMENTS

Figure 1:
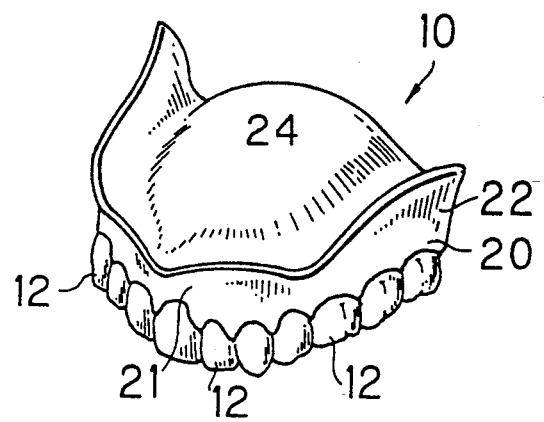
FIG. 1 is a perspective view of the maxilliary denture formed of a photopolymerizable denture base material in accordance with the present invention.

A prosthetic denture precursor 10 includes at least one artificial tooth 12 having a root portion 14 and a base member 20 holding the root portion of the tooth. Artificial which compose all or a part of a mandibular or maxillary set may be assembled in connection with the base member 20.

An artificial tooth 12 may have a shape corresponding to any of a human tooth such as a molar, a bicuspid, a cuspid, an incisor, etc. An artificial tooth is provided with a bite portion for occlusion. A root portion 14 of the tooth 12 may not necessarily correspond to a shape of human teeth because the root portion is buried in the denture base 20.

Alternatively an artificial tooth may have a shape corresponding to two or more adjacent teeth combined, for example two or three adjacent molar teeth combined, so that it is easier to arrange such a combined artificial tooth onto a base member 20 consistent with an occlusion theory than to arrange each individual tooth.

A tooth 12 is preferably formed of any hard material such as an acrylic resin, a hard resin, a ceramic material, and a metallic material. Preferably a tooth 12 essentially consists of an acrylic resin, and such an acrylic tooth is commercially available.

When a ceramic tooth 12 or a metallic tooth 12 is employed, the tooth is connected to the base member 20 in a standard manner. For example, a tooth 12 for an incisor or a cuspid may be connected to the base member 20 through two parallel pins. A tooth 12 for a molar may have a cavity in its bottom and a pair of lateral holes that are connected to the cavity and that through the opposite side of the wall surrounding the cavity so that a dental base material fills the cavity and the lateral holes so as to connect the tooth 12 to the base member 20.

The base member 20 generally has a U shape to conform the usual edentulus ridge of patients' mouths. A base member 20 includes a labial flange 21 in front. A base member includes buccal flanges 22 at both sides of the base member 20, and the buccal flanges 22 extends from the labial flange 21. The flanges 21 and 22 support artificial teeth 12. A base member 20 may have a palate plate 24, which laterally extends from the labial flange 21 and both of the buccal flanges 22.

A base member 20 is formed of a deformable photopolymerizable material which is as soft as a dough and which keeps its softness during procedures to fit occlusion so that a dentally operative position of a tooth in a denture precursor is adjustable by manually sliding or twisting the tooth 12 on the base member 20 with a custom mold 45 of a patient's mouth.

The photopolymerizable material for a base member 20 irreversibly hardens upon exposure to light so that a tooth 12 is rigidly fixed to the hardened base member 20. Preferably a photopolymerizable material does not change its shape or its volume before and after a hardening process.

Preferably exposure to visible light from a visible light source makes the photopolymerizable material harden. Preferably the photopolymerizable material has properties such that it hardens by irradiation of visible light for 30 seconds to 10 minutes. It is more favorable that the photo reaction time ranges from 30 seconds to 3 minutes.

Such a photopolymerizable material may have a composition including an uncured or semi-cured photopolymerizable acrylic resin. The term "acrylic" is used in its broadest sense to include the group of resins that may contain any of the following monomers, their oligomers, or their polymers: methylmethacrylate, ethylmethacrylate, triethylene glycol dimethacrylate, diethylene glycol dimethacrylate, ethylene glycol dimethacrylate, 2, 2-bis[4-(2-hydroxy-3-methacryloxypropoxy)-phenyl]propane, and di(methacryloxy)trimethylhexamethylenediurethane.

Preferably a photopolymerizable material contains about 0.1 to 5% by weight of a photo sensitizer and/or a reducing agent so as to control the reactivity of the composition in photochemical reactions. A photo sensitizer may be known compounds that include camphorquinone, diacetyl, $\alpha$-naphtyl, $\beta$-naphtyl, etc. Examples of reducing agents include N,N-dimethylaminoethylmethaerylate, N-phenylglycine, p-dimethylaminobenzoic acid, etc.

A photopolymerizable material may also contain other fillers and reinforcing agents such as amorphous silica, powdered quartz, etc.

As an advantage of the use of a photopolymerizable material to compose a denture base member 20 in the denture precursor 10, once the photopolymerizable material hardens, the hardened material does not change its shape any longer. In contrast, even after a hardening or a curing step, a thermally deformable acrylic resin or a thermally polymerizable material may change its shape again by heat. Moreover, a shape of a thermally polymerizable material may change during a polymerization process also. Besides, unreacted monomers in the thermally polymerizable material might be scattered around during a polymerization process. Lastly before a hardening process, a photopolymerizable material can undergo a long period of storage in a bag that does not pass light.

Preferably an artificial tooth 12 is formed of an acrylic resin, and a photopolymerizable denture base material to constitute a base member 20 has a composition including a photopolymerizable acrylic resin having a polymerizable component, such as monomers or oligomers of some derivatives of acrylic acid or methacrylic acid, so that a part of the polymerizable component is able to diffuse into the acrylic tooth 12. Upon exposure to light the polymerizable component diffused into the acrylic tooth 12 is polymerized along with the polymerization or hardening of denture base member 20 so that the acrylic tooth 12 is chemically bonded to the hardened denture base member 20.

Figure 2:
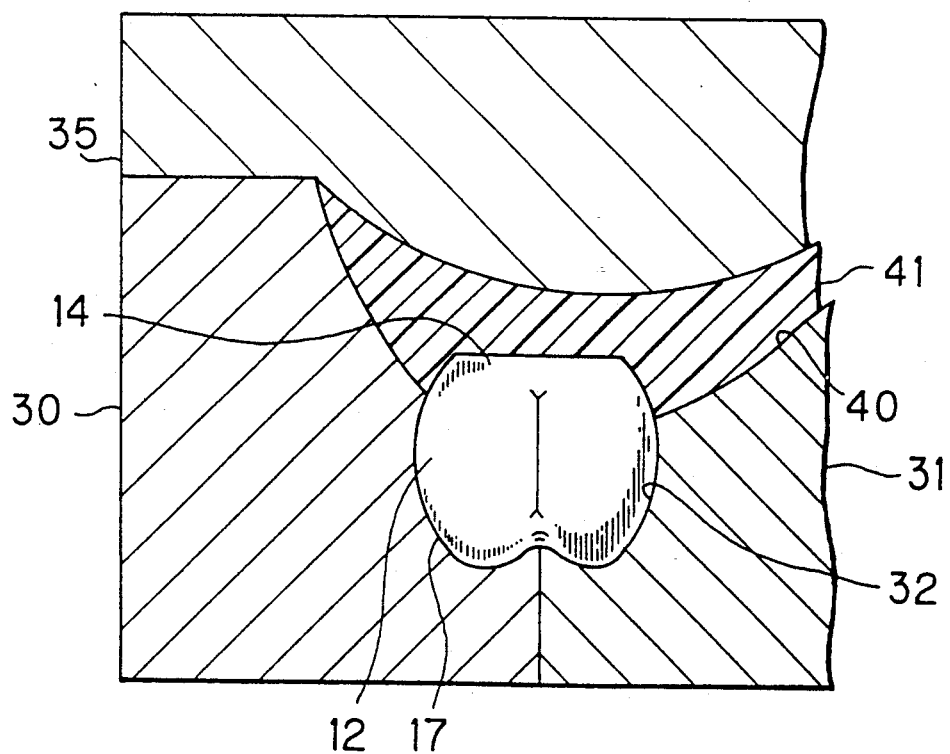
FIG. 2 is a cross-sectional view of the prosthetic denture precursor in accordance with the present invention.
Figure 3:
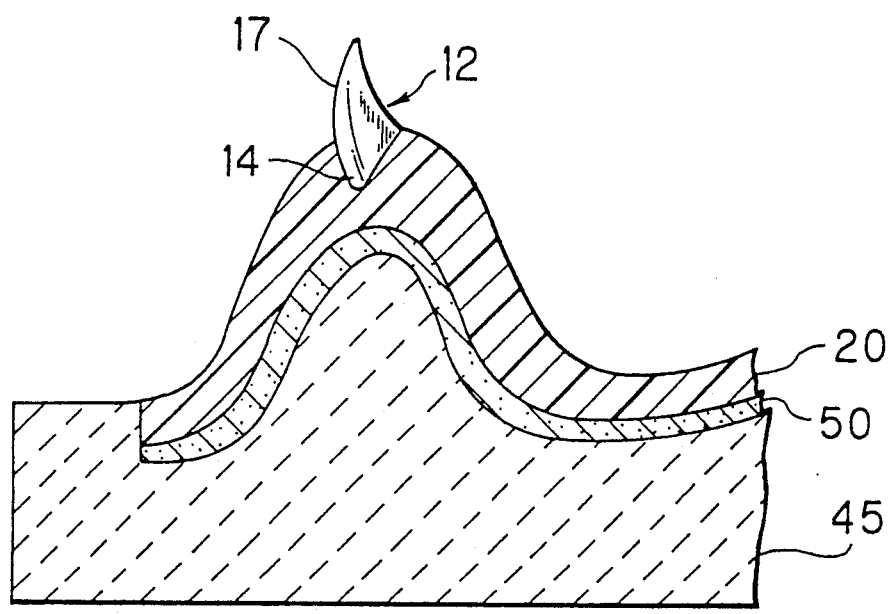
FIG. 3 is a partial cross-sectional view of a denture precursor, a spacer, and a custom mold in accordance with the method of the present invention.

A method for manufacturing and using a prosthetic denture precursor is described hereinafter. In accordance with the method of making a prosthetic denture precursor, crown portions 17 of artificial teeth 12 are held in U-shaped cavities 32 in two lower molds 30, 31 that conform to an average arrangement and spacing of human teeth (FIG. 2). The U-shaped cavities are formed along the junction of the two lower molds 30, 31. It should be avoided to employ a single lower mold that would create undercut cavities having shapes of such teeth as molars.

Recesses 40 are provided between an upper mold 35 and the two lower molds 30, 31, and an uncured photopolymerizable doughy resin 41 is placed on the recesses 40 in the lower molds 30, 31 to completely fit to the mold contour. At this point the resin covers over the root portions of the artificial teeth 12 in the cavities 32. The photopolymerizable doughy resin 41 may be an acrylic resin, which may have a composition, for example, comprising 50 parts of urethanedimethacrylate, 50 parts of hexamethylene glycol dimethacrylate, 2 parts by weight of camporquinone or camphane-2,3-dion, and 2 parts by weight of dimethylaminoethylmethaerylate.

The surface of an upper mold 35 that contacts the resin 41 in the recesses 40 is preferably coated with a release agent so that the coating on the surface facilitates the upper mold 35 from separating from the completed denture precursor 10.

Then an upper mold 35 is pressed into mating engagement with lower molds 30, 31 to form the photopolymerizable material into a denture base member 20 having the tooth 12 embedded therein. The upper mold 35 is removed, and a denture precursor 10 thus obtained is taken out.

When an artificial tooth 12 is formed of an acrylic resin and when a photopolymerizable denture base material has a composition including a photopolymerizable acrylic resin having a polymerizable component, such as monomers or oligomers of some derivatives of methacrylic acid, a part of the polymerizable component is able to diffuse into the acrylic tooth 12.

It has been found that shapes, sizes, and spacings of human mouths do not vary in a wide range, and thus a limited number of selected sizes in the denture precursor 10 suffice to cover the range of physical variances commonly found in the human mouth. Therefore, a dentist can select a size of a denture precursor closest to each patient's mouth.

In accordance with the method of using a denture precursor, i.e. a method of preparing a prosthetic denture device, a custom mold 45 formed of an appropriate material such as gypsum is used. The custom mold 45 has a shape conforming to an impression of a patient's mouth, and the custom mold 45 is prepared in a standard known procedure.

A plastic material is placed on the custom mold 45 so that a plastic material forms an integral spacer 50 having a U shape corresponding to the edentulus ridge of a patients' mouth. Clay is favorably used as a plastic material with water as a binder. However, a binder may be silicone as well as fats and oils. A plastic material refers to any material that is plastic and it includes, for example, a plastic material made by kneading starch with water.

A denture precursor 10 having unhardened photopolymerizable denture base 20 is mounted on the spacer 50 in contact with the custom mold 45. Preferably a sheet separates the denture precursor 10 from the spacer 50 so that a plastic material that composes the spacer 50 does not stick to the surface of the denture base 20 contacting the spacer 50. The sheet may be a man-made plastic sheet, such as a polyethylene sheet.

A position, a direction, and a depth of the tooth 12 are adjusted to a dentally operative position. Preferably the denture base member 20 is adjusted to conform to the spacer 50. However, the surface on the denture base member 20 contacting the spacer 50 does not have to exactly or carefully conform to the contacting surface on the spacer 50 because the surface on the denture base member 20 contacting the spacer 50 does not lead to a surface in the resulting complete denture. Instead the surface on the denture base member 20 contacting the spacer 50 is covered with a resin material in a later step to make a denture device.

Visible light from a visible light source is irradiated on the base member 20 in a denture precursor 10 for a given time depending on the base material 20 so that the base member 20 irreversibly hardens and so that a tooth 12 is rigidly fixed to the hardened denture base 20. A visible light source is not restricted, and the source may be a xenon lamp, a halogen lamp, a tungsten lamp, etc. For example, a light source under the trade name "DENTACOLOR XS" from Kulzer Company may be used for this purpose.

A position of the light source may be moved around the base member 20 to provide any surface of the base member 20 with enough light to harden. The base material 20 may not necessarily undergo a continuous irradiation, and irradiations may have interruptions.

When an artificial tooth 12 is formed of an acrylic resin and when a photopolymerizable denture base material has a composition including a photopolymerizable acrylic resin having a polymerizable component, upon exposure to light the polymerizable component diffused into the acrylic tooth 12 is polymerized along the polymerization or hardening of photopolymerizable denture base member 20 so that the acrylic tooth 12 is chemically bonded to the hardened denture base member 20.

The hardened denture precursor 10 is set aside, and the spacer 50 formed of the plastic material is removed. The custom mold 45 may be washed by an appropriate liquid, such as water, to remove the residual plastic material on surfaces of the custom mold 45.

The washed denture precursor 10 is mounted back onto the washed custom mold 45 so as to leave the recess which was occupied by the spacer 50 between the precursor 10 and the mold 45. Into this recess is carefully placed a doughy resin material so that the resin material completely conforms to the contours of both the custom mold 45 and the denture base 20 forming the recess. The resin material is placed so as to completely conform to the contours of the mold 45 because the surface on the resin material contacting the mold 45 leads to a surface in the resulting complete denture contacting a human mouth. The resin material is placed to completely conform to the contours of the denture base 20 so as not to leave inclusion of air as fine pores in the denture base member in the resulting denture device.

The resin material has properties such that it hardens by heat or light. Preferably the resin material does not change its shape or its volume before and after a hardening process.

This resin material may be an acrylic resin that undergoes thermal polymerization at temperatures ranging from room temperature to 50° C., for example, an acrylic resin having heat shock resistance and a self-curing acrylic resin. These types of acrylic resins are commercially available. Alternatively the resin material may be a photopolymerizable material described above.

Then the resin material in the recess is hardened by an appropriate method according to its property so that the hardened resin material is bonded to the denture base 20 to form an integral denture base member 20, and a prosthetic denture device is made.

It is important to use the invented denture precursor to perform the method of the present invention to have a satisfactory accuracy in the shape of the denture device. To show its importance, a denture device was made by a method similar to the method of the present invention that does not use the denture precursor according to the present invention.

As a control experiment a photopolymerizable acrylic resin material was placed on a mold of a human mouth, which is commercially available under the product name of 500A from Nisshin Inc. from Tokyo. The photopolymerizable acrylic resin material, for example, may be a product under the trade name of TRIAD from Dentsply Inc. and another product under the trade name of EPOREX-D from NOF Corporation (Nihon Yushi) from Tokyo.

A denture base structure essentially consisting of the photopolymerizable acrylic resin material, was formed on the mold of a human mouth. To form the base structure, unnecessary resin material was removed, and some resin material was added to a necessary part of the structure. Artificial acrylic teeth were manually inserted into the base structure to be arranged into a dentally operative position. The photopolymerizable acrylic resin material was irradiated by visible light from a visible light source under the trade name DENTACOLOR XS from Kulzer Company for 90 seconds, and the material was polymerized and hardened to give a denture device.

The denture device thus obtained had dents due to air around the root portions of some artificial acrylic teeth and some portions between two adjacent teeth in its denture base member.

Moreover, the complete denture device in control contained fine pores, caused by inclusion of air, in some parts of its denture base member which corresponded to junctions made by additional resin material.

Furthermore, artificial acrylic teeth in the complete denture device in control were not chemically bonded to the hardened denture base member because artificial acrylic teeth in control had a limited time to be in contact with the photopolymerizable acrylic resin material so that a sufficient amount of monomers in the acrylic resin material did not diffuse into the acrylic teeth for the polymerization.

In contrast, such dents around the root portions or fine pores in junctions did not form in the denture precursor 10 according to the present invention because a denture base material is pressed against an artificial tooth 12 in molds 30, 35, 36. When artificial acrylic teeth are used in the denture precursor 10, the acrylic teeth 12 in the complete denture device are chemically bonded to the hardened denture base member 20.

It will be appreciated that the present invention provides simplified procedures to make a prosthetic denture device without making a wax denture and that the denture device thus made still has an accuracy as much as the one made in the conventional method via a wax denture.

Moreover, a prosthetic denture precursor according to the present invention does not require procedures to handle the precursor for its fitting inside a patient's mouth because a prosthetic denture device obtained by the method of the present invention has a shape which is compliment to a custom mold prepared from a patient's mouth.

It is to be understood that various alterations, modifications and/or additions may be made to the features of the possible and preferred embodiments of the invention as herein described without departing from the scope of the invention as defined in the claims.

What is claimed is:

1. A method for manufacturing and using a prosthetic denture precursor comprising:
  a. manufacturing a denture precursor including the steps of:
    placing a photopolymerizable material and at least one artificial tooth having a root portion in at least one mold, said photopolymerizable material being deformable; and
    forming said photopolymerizable material into a denture base having said at least one tooth embedded therein to form a denture precursor and removing said denture precursor from the mold;
  b. using said denture precursor including the steps of:
    placing said denture precursor in contact with a spacer which is in contact with a custom mold;
    adjusting said at least one tooth to a dentally operative position;
    irreversibly hardening said denture base by exposure to light so that said at least one tooth is rigidly fixed to the hardened denture base;
    removing the spacer from the custom mold to form a recess therein and placing a resin material into the recess which was occupied by the spacer so that said resin material conforms to both the custom mold and said denture base in said denture precursor; and
    hardening said resin material so that said resin material integrates into said denture base.

2. A method for manufacturing and using a prosthetic denture precursor comprising:
  a. manufacturing a denture precursor including the steps of:
    placing a photopolymerizable material and at least one artificial tooth having a root portion in at least one mold to form a denture precursor, said tooth containing an acrylic resin, said photopolymerizable material being deformable, said photopolymerizable material having a composition including a photopolymerizable acrylic resin having a polymerizable component;
    forming said photopolymerizable material into a denture base having said at least one tooth embedded therein so that a part of the polymerizable component is able to diffuse into said at least one tooth and removing said denture precursor from the mold; and
    standing the denture precursor for a sufficient time so that the polymerizable component diffuses into said at least one tooth;
  b. using said denture precursor including the steps of:
    placing said denture precursor in contact with a spacer which is in contact with a custom mold;
    adjusting said at least one tooth to a dentally operative position;
    irreversibly hardening said denture base by exposure to light so that said at least one tooth is rigidly fixed to the hardened denture base and so that said at least one tooth is chemically bonded by polymerization of the polymerizable component to the hardened denture base;
    removing the spacer from the custom mold to form a recess therein and placing a resin material into the recess which was occupied by the spacer so that said resin material conforms to both the custom mold and said denture base in said denture precursor; and
    hardening said resin material so that said resin material integrates into said denture base.

* * * * *